US010231936B2

(12) United States Patent
Prater et al.

(10) Patent No.: US 10,231,936 B2
(45) Date of Patent: Mar. 19, 2019

(54) DELAYED RELEASE PHARMACEUTICAL FORMULATIONS

(75) Inventors: Derek Allan Prater, Cambridgeshire (GB); Mohammed Hassan, Cambridgeshire (GB); Christopher Robert Bland, Kent (GB)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 11/603,766

(22) Filed: Nov. 22, 2006

(65) Prior Publication Data

US 2007/0071820 A1 Mar. 29, 2007

Related U.S. Application Data

(63) Continuation of application No. 10/399,077, filed as application No. PCT/GB01/04423 on Oct. 4, 2001, now abandoned.

(30) Foreign Application Priority Data

Oct. 13, 2000 (GB) .................................. 0025208.0

(51) Int. Cl.
*A61K 9/26* (2006.01)
*A61K 9/50* (2006.01)
*A61K 9/16* (2006.01)

(52) U.S. Cl.
CPC .......... *A61K 9/5073* (2013.01); *A61K 9/1652* (2013.01); *A61K 9/5026* (2013.01); *A61K 9/5036* (2013.01)

(58) Field of Classification Search
None
See application file for complete search history.

(56) References Cited

U.S. PATENT DOCUMENTS

| 4,687,660 | A | | 8/1987 | Baker et al. | |
|---|---|---|---|---|---|
| 4,844,910 | A | | 7/1989 | Leslie et al. | |
| 4,871,549 | A | | 10/1989 | Ueda et al. | |
| 5,151,273 | A | | 9/1992 | Korsatko-Wabnegg et al. | |
| 5,188,841 | A | | 2/1993 | Husson et al. | |
| 5,593,697 | A | | 1/1997 | Barr et al. | |
| 5,980,942 | A | * | 11/1999 | Katzhendler et al. | 424/465 |
| 6,068,859 | A | * | 5/2000 | Curatolo et al. | 424/490 |
| 6,156,343 | A | | 12/2000 | Morita et al. | |
| 6,358,528 | B1 | * | 3/2002 | Grimmett et al. | 424/474 |
| 2009/0270463 | A1 | | 10/2009 | Kobayashi et al. | |

FOREIGN PATENT DOCUMENTS

| CA | 2028633 A1 | 4/1991 | |
|---|---|---|---|
| CA | 2368367 | 10/2000 | |
| EP | 171457 | 2/1986 | |
| EP | 0220143 A1 | 4/1987 | |
| EP | 312340 | 4/1989 | |
| EP | 347024 | 12/1989 | |
| EP | 409254 | 1/1991 | |
| EP | 425298 | 5/1991 | |
| EP | 0527638 | * 2/1993 | ............ A61K 31/55 |
| EP | 527638 | 2/1993 | |
| EP | 797991 | 10/1997 | |
| EP | 1121931 | 8/2001 | |
| JP | 61-053214 | 3/1986 | |
| JP | 63-215620 | 9/1988 | |
| JP | 8-26977 A | 1/1996 | |
| JP | 8-143476 A | 6/1996 | |
| JP | 9-104620 | 4/1997 | |
| JP | 2001-55322 A | 2/2001 | |
| WO | 96/40628 | 12/1996 | |
| WO | 98/47869 | 10/1998 | |
| WO | 2000/020000 | 4/2000 | |

OTHER PUBLICATIONS

Ueda et al (Development of a novel drug release system, time-controlled explosion system (TES). II. Design of multiparticulate TES and in vitro drug release properties. Chem Pharm Bull. 42(2): 359-363 (1994)).*
Banjanac et al (Anti-inflammatory mechanism of action of azithromycin in LPS-stimulated J774A.1 cells. Pharmacol Res. Oct. 2012;66(4):357-62).*
Banga, JA et al. "Systemic Delivery of Therapeutic Peptides and Proteins" *Intl. J. Pharmaceutics* 48: 15-50 (1988).
Davis, S.S., et al. "A comparative-study of the gastrointestinal transit of a pellet and tablet formulation." *International Journal of Pharmaceutics* 21 167-177, 1984.
Fix, JA "Oral controlled release technology for peptides: status and future prospects." *Pharm Res.* Dec. 1996;13(12):1760-4.
Fu et al. "Preparation and in vito release of 5-aminosalicylic acid time-controlled release pellets for colon-specific delivery" CAS 133: 48839x (*Yaoxue Xuebao* 35(5): 389-393) (2000).
Ishibashi et al., "Design and Evaluation of a New Capsule-Type Dosage Form for Colon-Targeted Delivery of Drugs", *Int'l J. of Pharmaceutics* 168: 31-40 (1998).
Krogel I et al. "Pulsatile drug release from an insoluble capsule body controlled by an erodible plug". *Pharm Res.*;15(3):474-81. (Mar. 1998).
Lemmer B. "Chronopharmacological aspects for the prevention of acute coronary syndromes". *Eur Heart J.* 19 Suppl C: C50-8. (Apr. 1998).
Lemmer B. "Circadian rhythms and drug delivery" *Journal of Controlled Release* 16: 63-74 (1991).
Morita R, et al., "Development of oral controlled release preparations, a PVA swelling controlled release system (SCRS)—I. Design of SCRS and its release controlling factor" *Journal of Controlled Release*, 63(3): 297-304 (2000).

(Continued)

*Primary Examiner* — Jake M Vu
(74) *Attorney, Agent, or Firm* — Sterne, Kessler, Goldstein & Fox P.L.L.C.

(57) ABSTRACT

Delivery of a drug is controlled to impart a delay before release after administration by formulating the drug with a disruption agent to provide a core, and coating the core with a regulatory membrane comprising a water-soluble gel-forming polymer and a water-insoluble film-forming polymer.

23 Claims, 7 Drawing Sheets

(56) References Cited

OTHER PUBLICATIONS

Narisawa S et al., "An organic acid-induced sigmoidal release system for oral controlled-release preparations" *Pharm Res.*;11(1):111-6. (1994).

Narisawa S et al., "An organic acid-induced sigmoidal release system for oral controlled-release preparations. III. Elucidation of the anomalous drug release behavior through osmotic pumping mechanism" *International Journal of Pharmaceutics*, 148(1): 85-91 (1997).

Pozzi et al., "The Time Clock System: A New Oral Dosage form for Fast and Complete release of Drug After a Predetermined Lag Time," *Journal of Controlled Release*, 31: 99-108 (1994).

Santus G, et al., "Osmotic drug delivery: a review of patent literature". *J Control. Release.*;35:1-21 1995.

"Scherer DDS develops "alarm clock" dose formulation" *Pharm. J.* 247: 138 (1991).

Ueda, et al., "Development of a novel drug release system, time-controlled explosion system (TES)", *Journal of Drug Targeting*, 2(1): 35. (Abstract only) (1994).

Ziv et al, "Oral administration of insulin in solid form to nondiabetic and diabetic dogs",. *J Pharm Sci* 83(6): 792-794.

"Hydroxypropyl Methylcellulose" in *Handbook of Pharmaceutical Excipients* 4$^{th}$ ed. p. 229 (2003).

Methocel E15 Product Specification, Colorcon (2005).

Methocel K100M Product Specification, Colorcon (2005).

"Methyl cellulose" from ROMPP, Lexicon der Chemie, Georg Thieme Verlag, Stuttgart (1995).

"Low-substituted hydroxypropylcellulose" (printout from Shin-Etsu Chemical Co., Ltd., homepage dated Jan. 2, 2005).

Voigt, *Lehrbuch der pharmazeutischen Technologie* 5$^{th}$ ed., Verlag Chemie (1987) pp. 692-693.

Practical pharmaceutical additive *Chemical Industry Co.*, (1974) pp. 106-107 (Engl. Translation).

Schultz, P et al., "A new multiparticulate delayed release system. Part I: Dissolution and release mechanism" *Journal of Controlled Release* 47(2): 181-189 (1997).

Schultz, P et al., "A new multiparticulate delayed release system. Part II: Coating formulation and properties of free films" *Journal of Controlled Release* 47(2): 191-199 (1997).

Ueda, S et al., "Development of a novel drug release system, time-controlled explosion system (TES). II. Design of multiparticulate TES and in vitro drug release properties" *Chem. Pharm. Bull.* 42(2): 359-363 (1994).

Pharmacoat specification (printed from ShinEtsu webpages on Jan. 31, 2005).

English language abstract of JP 8-26977 A, espacenet database, Worldwide, published Jan. 30, 1996.

English language abstract of JP 8-143476 A, espacenet database, Worldwide, published Jun. 4, 1996.

English language abstract of JP 2001-55322 A, espacenet database, Worldwide, published Feb. 27, 2001.

Committee for Proprietary Medicinal Products (CPMP), "Note for Guidance on Quality of Modified Release Products: A: Oral Dosage Forms; B: Transdermal Dosage Forms. Section 1 (Quality)," The European Agency for the Evaluation of Medicinal Products—Human Medicines Evaluation Unit, London, England (Jul. 29, 1999).

Ferry, J.D., *Viscoelastic Properties of Polymers, 3$^{rd}$ Edition*, p. 529, John Wiley & Sons, Inc., United States (1980).

Food and Drug Administration. Center for Drug Evaluation and Research (CDER), "Guidance for Industry—SUPAC-MR: Modified Release Solid Oral Dosage Forms," U.S. Department of Health and Human Services, United States (Sep. 1997).

Dow Website, "METHOCEL™ Products," 1 page, accessed at http://www.dow.com/dowexcipients/products/methocel.htm, accessed on Feb. 12, 2009.

"METOLOSE®," 24 pages, Cellulose & Pharmaceutical Excipients Department, Shin-Etsu, Japan (2009).

"PHARMACOAT®," 16 pages, Cellulose & Pharmaceutical Excipients Department, Shin-Etsu, Japan (2009).

Witness Statement of Dr. Hassan Mohammad in the matter of an Appeal by EURO-CELTIQUE S.A. against the decision to refuse European Patent Application No. 01972310.5 in the name of EURO-CELTIQUE S.A.. 5 pages, dated Dec. 3, 2009.

Decision Rejecting the Opposition for European Patent Application No. EP 01972310.5, dated May 16, 2018, European Patent Office, Netherlands, 11 pages.

Ragnarsson, G., et al., "In vitro release characteristics of a membrane-coated pellet formulation—influence of drug solubility and particle size," *International Journal of Pharmaceutics* 79:223-232, Elsevier Science Publishers B.V., Netherlands (1992).

\* cited by examiner

DELAYED RELEASE PHARMACEUTICAL FORMULATIONS

This application is a continuation of U.S. patent application Ser. No. 10/399,077, filed on Sep. 30, 2003, which claims priority to Great Britain Patent Application No. 0025208.0, filed Oct. 13, 2000 through International Application No. PCT/GB01/04423, filed Oct. 4, 2001.

This invention relates to pharmaceutical preparations and especially to delayed release pharmaceutical preparations. More particularly, the present invention relates to delayed release pharmaceutical formulations which release a drug after a delay following administration to a patient. Preferred formulations may release the drug rapidly after such a delay.

BACKGROUND OF THE INVENTION

The development of chronobiological knowledge, as described for example by Lemmer in Journal of Controlled Release 16 (1991) 63-74 and Lemmer, European Heart Journal (1998) 19 (Supplement C) C50-C58, has led to an interest in chronotherapeutics, which is the release of a drug in the body in synchronisation with the biological rhythm. The role of circadian rhythms in the function of the body and hence the therapeutic needs have in particular been investigated. Cardiovascular activity, pulmonary, hepatic, gastrointestinal and renal functions are all known to follow circadian rhythms, and for instance, gastric motility, gastric pH, and enzymatic secretion vary during the day. Given that hepatic and renal activity also vary, then it follows that absorption, metabolism and excretion can be expected to follow the same pattern. The therapeutic and toxic effect of drugs can therefore display a significant variation during the course of a day. It is preferable that the biological rhythms be taken into consideration when a new drug delivery system is developed.

The goal is to design a system that allows drug delivery to be decoupled from the act of drug administration and to be synchronised with the biological rhythm, in accordance with chronotherapeutics. Drug administration can then occur at a convenient time, rather than at a time dictated by drug delivery.

To address such needs, a triggered, pulsed or programmed drug delivery system is more suitable, rather than a conventional normal release or controlled release dosage form. This system might provide one or more of the following advantages:

produce maximum benefits with minimum side effects;
avoid drug tolerance;
overcome a saturable first pass loss via the gastrointestinal tract;
reduce dose frequency and dose level and thus increases patient compliance;
deliver the drug at the time most needed.

Some delayed release dosage forms are already known. Mechanical disruption of a delayed release coat provides one mechanism for a delayed release system. In one proposal, a formulation is made comprising a core containing a drug and a swelling agent, coated with a water-insoluble but permeable polymer, see Ueda et al. in Journal of Drug Targetting, 1994, 2, 35-44. After the device is orally administered, water permeates into the core, which hydrates and swells. The stress caused by the swelling ruptures the coating to enable drug release. In a variation different fillers were used, including an effervescent agent, which were filled into capsules and coated with water-insoluble polymers.

Santus G and Baker R, 1995, Journal of Controlled Release 35 (1995) 1 reviewed the literature using the concept of osmotic pressure in controlling the drug release. Single unit devices such as tablets, hard and soft capsules and other mechanical osmotic pumps were reviewed and analysed. The authors concluded that osmotic systems could be used effectively to determine the time and the rate of the drug release. Thus, the swelling agent in the core is replaced with an osmotic agent and the core is coated with a semipermeable membrane. Osmotic pressure thus exerts a stress on the membrane, rupturing it and so resulting in a rapid release of the drug. This technology is suitable for devices having a low surface area/volume ratio such as single unit dosage forms for example tablets.

Another type of delivery system relies on hydration or erosion. A notable example consists of a water insoluble capsule filled with a drug plugged with a hydrogel and covered with a water-soluble cap. After the capsule is orally administered the cap dissolves and the hydrogel plug becomes fully hydrated after a certain time and is expelled, thereby permitting a rapid and complete release of the drug. Such a device referred to as the Pulsincap™ device was disclosed by Scherer DDS in 1991, see Pharma. J., Vol. 247, 138. An alternative pulsatile drug release system is described by Krogel and Bodmeier in Pharmaceutical Research, 1998, 15, 474, using an erodible plug formed by compression or from a melt as a closure to an impermeable capsule body.

Yet another delivery system based on hydration and erosion is that described by Pozzi et al. in Journal of Controlled Release, 1994, 31, 99-108. The device is a solid core coated with a hydrophobic-surfactant layer, applied as an aqueous dispersion, to which a hydrosoluble polymer is added to improve adhesion to the core. The coating rehydrates and redisperses in an aqueous environment in a time proportional to the thickness of the film. Thus the coat has been designed to be completely removed after a pre-determined lag time depending on the coat thickness. The different physiological and chemical environment through the gastrointestinal tract are not expected to alter significantly the releasing time.

A further delayed release system comprises a solid core of drug an organic acid such as succinic acid and coated with a thick coat of Eudragit RS, see Narisawa et al, 1994, Pharm. Res. Vol. 11, 111 and Narisawa et al. International Journal of Pharmaceutics 148 (1997) 85-91. Eudragit RS is a copolymer synthesised from acrylic and methacrylic acid esters with a low level of quaternary ammonium groups. The film formed by this polymer is water insoluble with low permeability. On full hydration, water gradually penetrates the membrane into the core and dissolves the organic acid. The resulting polymer/acid interaction induces a structural change in the coating film, increasing permeability, which enhances the drug release.

A similar approach to the above is described in Ishibashi et al. International Journal of Pharmaceutics, 168 (1998) 31-40. This device comprises a blend of drug and organic acid made into solid cores which are filled into gelatin capsules. The capsule is coated with three different polymeric layers; an inner layer consisting of cationic polymer dissolving in acidic fluid, a water-soluble intermediate layer, and an outer layer consisting of enteric materials dissolving at pH above 5. The intermediate layer serves to prevent direct contact between the inner and outer layers. The predicted performance of this product is that drug release is prevented in the stomach by the outer polymeric layer, after gastric emptying the outer and intermediate layers quickly dissolve but the inner polymeric layer remains to prevent drug release in the intestine, and then when the pH inside the capsule gradually decreases with dissolution of the organic acid and the inner polymeric layer is dissolved by the acidic fluid, the drug content is quickly released.

One simple approach to delaying the release of drug relies solely on the enteric behaviour of some polymers whereby the delay is dependent upon gastric residence time. Devices of this kind, which may comprise tablets capsules, spheroids and beads, can be coated with polymers that dissolve only in a medium of pH 5 or higher. The coated core will survive the low pH in the stomach and release its contents rapidly in the alkaline environment of the upper part of the intestine.

Systemic delivery of therapeutic peptides and proteins via the colon may be achieved way from a delayed release dosage form. Recently, the unprecedented rapid development of biotechnology and genetic engineering has resulted in the availability of a significant number of peptides and proteins at a reasonable price. Colonic delivery has attracted much interest, see for example Banga and Chien in International Journal of Pharmaceutics, 48 (1988) 15-50; Fix in Pharmaceutical Research, 13 (1996) 1760; and Ziv et al., Journal of Pharmaceutical Sciences, 83 (1994) 792. Among several routes intensively studied is colonic delivery because of the low activity of pancreatic erzymes, the reduced brushborder membrane peptidase activity and the avoidance of liver first pass.

The available technologies for delayed release pharmaceutical compositions have a number of disadvantages. The development of a system which is independent of the physiological condition of the gastrointestinal tract, unaffected by fed and fast condition of the patients offers a considerable challenge.

An object of the present invention is to provide a pharmaceutical composition which is capable of delayed and then rapid release of the active ingredient.

SUMMARY OF THE INVENTION

According to the present invention there is provided a delayed release pharmaceutical composition. With such a composition there is a delay or lag in the delivery of drug following administration.

The composition comprises a core which includes a drug and a disruption agent. There is a regulatory membrane coating on the core formed from a mixture of a water-soluble gel-forming polymer and a water-insoluble film-forming polymer.

The water-insoluble film-forming polymer forms a film coating on the core together with the water-soluble gel-forming polymer and serves to regulate the entry of water. Without being bound by theory, it is surmised that after administration of the composition to a patient there is a delay while gastric and other fluids hydrate the water-soluble polymer of the regulatory membrane coating to form a gel. With the passage of time, this gel is then gradually dissipated to allow fluid to reach the disruption agent and bring about rupture, stretching or other disruption of the integrity of the remaining membrane. With this loss of integrity, there is release of the drug. This theory might explain how it is possible to provide, for instance, a delayed release for say at least one or two hours and then a rapid and complete release over a predetermined number of following hours.

Preferred Embodiments

The composition may be a unitary dosage form such as a tablet or lozenge but is preferably a multi-unit dosage form comprising multiparticulates, for instance beads or spheroids. The multiparticulates may be contained in a-capsule such as a hard gelatin capsule or a sachet, or may be formed into tablets by compression.

It is generally considered that high surface area/volume ratio multiparticulates are not suitable for the available delayed release technology. To delay the water permeation into the multiparticulate cores, a water regulating membrane is provided by the present invention. The pressure exerted from the disruption agent is then sufficient to disrupt the remaining membrane after full hydration.

Examples of suitable disruption agents for the compositions of this invention include polymers with the capacity to expand on hydration, such as low substituted hydroxypropylcellulose (LH-11®, LH-21® and LH20®, Shin-Etsu Chemical, Japan), sodium starch glycolate (Explotab®, Edward Mendell USA), sodium carboxymethylcellulose-croscarmellose sodium (Ac-Di-Sol® FMC USA), and carbomers (Carbopol® 971p and Carbopol® 974p BF Goodrich, US).

Further examples of suitable disruption agents include compounds which can generate an internal osmotic pressure within the membrane, such as sodium chloride, magnesium sulphate and other electrolytes or sucrose, mannitol, other sugars and polyhydric alcohols.

The need for expansion or osmotic agents can possibly be eliminated when a high load of water-soluble drug is used, since a water-soluble drug might act as an osmotic agent to generate the required internal pressure on hydration.

In addition to the disruption agent and drug, the cores may also include one or more conventional excipients. In the case of spheroids, such excipients may include spheronisation aids such as microcrystalline cellulose (Avicel PH 101) and binders such as hydroxypropylmethylcellulose. Alternative spheronisation aids that may be used include other grades of microcrystalline cellulose, lactose and other sugars. Other release modifying agents such as surfactants (for example tween 80, and other ionic and non ionic surfactants).

The cores may have a diameter of 0.5 to 4.0 mm, preferably 0.5 to 2.0 mm, and more preferably 1.0 to 2.0 mm, before coating.

Preferably the cores contain 5 to 80% by weight of active substance and 0 to 50%, preferably 10 to 30%, by weight of swelling agent, or 0 to 50%, preferably 10 to 30%, by weight of osmotic agent. In the case of spheroids, spheronising aids and binders may be present in amounts conventionally required to achieve satisfactory spheronisation and may amount to 5 to 90% weight, for example spheroid cores may be prepared containing 5 to 90% by weight of spheronising agent such as microcrystalline cellulose and 0 to 1% by weight of binders.

The water-soluble gel-forming polymer of the regulatory membrane coating is preferably a high viscosity grade hydroxy alkyl cellulose such as hydroxypropylmethylcellulose (HPMC) or methyl cellulose.

The water-insoluble film forming polymer of the regulatory membrane coating is preferably an alkyl cellulose such as ethyl cellulose. Preferably the polymer provides pH-independent release.

The coating may contain water-soluble gel-forming polymer and water insoluble film-forming polymer in a wide range of ratios. In particular, changing the coating solution components and the coating level can also modify the lag time or delay time. Coating solution component ratios of 10:90-90:10, preferably 20:80-80:20 film-forming, water-insoluble polymer (ethyl cellulose):high viscosity grade gel-forming polymer (HPMC or methyl cellulose), with or without other ingredients such as lubricants and anti-tack agents including talc, magnesium stearate, glycerol monostearate and fused silica, can be effectively used to modify the release profile.

The lag time between the dosing and the onset of the release can also be modified by altering the amount of coat applied. As low as 2.5% or 10% to as high as 100% preferably 20-70% coating weight gain are required to produce the delay and release profile.

The coating may contain additionally conventional coating excipients such as plasticisers, for example triethyl citrate or dibutyl sebacate, anti-tack agents, for example talc, magnesium stearate, glycerol monostearate or fused silica, and non-ionic, anionic or cationic surfactants for example tween 80 or sodium lauryl sulphate, and other coat modifying agents.

In an aqueous medium such as in vitro dissolution medium or in viuo gastric fluid, it is believed that the water-soluble polymer hydrates typically to produce a thick gel. Continuing exposure to the aqueous medium might further hydrate the water-soluble polymer which gradually dissolves and is removed, leaving behind a porous network of the water-insoluble coat.

The time delay of the release of the active ingredient can be adjusted by varying the amount of the coating as well as the ratio of the water-soluble:water-insoluble polymer. Plasticizers, anti tacking agents and other coat-modifying agents such as surfactants can be also used to modify the lag time.

The rapid and essentially complete release of the drug is achieved by the mechanical stretching and preferably rupture of the coating as a result of the swelling or osmotic pressure caused by core hydration.

Preferred embodiments of the devices of the invention release substantially no active ingredient (say less than 10%, preferably less than 5%, more preferably less than 2% and most preferably less than 1%) in the lag period of up to 1 to 6 hours, preferably 1 to 4 hours and more preferably 1 to 2 hours. It is preferred that after the delay, substantially the entire content of the active ingredient (say more than 50%, preferably more than 75%, more preferably more than 90% and most preferably more than 95% or 99%) is released over a release period of not greater than 6 hours, more preferably over a period of up to 4 hours for example 1 to 4 hours, even more preferably up to 2 hours for example 1 to 2 hours. In one variation, there is controlled release of the drug, for example over a period of 2 to 12 hours.

In preferred embodiments using swelling agents, the composition of the core is preferably one which, when the core is fully hydrated, expands to 20% to 100% of its dry volume.

In a further embodiment, the invention also provides a method for preparing the compositions, which comprises coating a core containing a mixture of a drug and disruption agent with a mixture of a water-soluble gel-forming polymer and a water-insoluble film forming polymer.

The present invention is suited for many kinds of drugs. Examples of such drugs include hypnotics, anti-inflammatories, steroids, anthelmintics, antifungal, anti-cancers, proteins and peptides. Suitable hypnotics include Zolpidem, Zoplicone and Zalaplan; suitable anti-inflammatories include 5-aminosalicylic acid, diclofenac and indomethacin; suitable steroids include for example corticosteroids, preferably fluticasone, budesonide and prednisolone sodium metasulphobenzoate; anthelmintics, antifungals, anti-cancers, proteins and peptides.

Another class of suitable compounds include the compounds claimed in WO 96/40628, such as 4-(4'-fluorophenoxy)benzaldehyde semicarbazone. In the WO text the compounds are for treating central nervous system disorders, but WO 98/47869 describes their use for blocking sodium channels and for treating chronic pain.

In formulating products of this invention, active ingredient of 0.1-500 mg, preferably 1-100 mg can be loaded into the spheroid cores. The modified release components such as osmotic and/or expansion agents and the spheronization aids can be varied from 5-80% of the total weight of the spheroid cores.

One important application for a delayed delivery system is the delivery of a short acting hypnotic in the early morning. Several psychiatric disorders such as anxiety, depression, and abuse of drugs and alcohol are common causes of sleep disturbance which can result in early wakening. Short acting hypnotic drugs are frequently used for the treatment of anxiety and depression related insomnia. Zolpidem tartrate (5-10 mg) and Zopiclone (7.5-15 mg) are taken at bed time in a conventional normal release dosage form and are commercially available. These and other similar drugs have a rapid onset of therapeutic action with maximum peak plasma concentration within 2 hours and an elimination half-life in the region of 2 hours.

In the present invention a novel solid dosage form with a two hours delay of release followed by rapid and complete release over 2-3 hours is postulated to optimally deliver a suitable short acting sedative hypnotic drug. The delivery system can effectively control the lag time of the dosage form release and is unaffected either by the physiological condition of the gastrointestinal tract (for example pH, motility, residency time), the fed or fasting state of the patient, and by the waking or sleeping state of the patient. Thus, it is proposed that a delayed release dosage form of a short acting hypnotic is superior to that of a conventional, normal release one. The delayed release dosage form is designed to be taken before retiring to bed but releases the drug at the time most needed for instance before waking in the early hours of the morning. This type of dosage form might provide the following advantages over that of a conventional normal release one:

Lower dose is required—the patient receives the drug before waking

Lower dose means lower toxicity, improved tolerance, and less hangover symptoms in the morning Another example is to suit the biological rhythm of the gastric section. $H_2$-blockers such as cimetidine, ranitidine, might be delivered to ensure that they achieve maximal effect in the afternoon when acid secretion is at its highest.

Nocturnal asthma is a very common event in asthmatic patients, therefore it is advisable to deliver asthmatic drugs such as theophylline in the early hours before the normal waking time. A delayed release composition of this invention can will provide the required amount of the drug at its maximum needed time.

Beta-blockers, and calcium channel blockers, in general reduce high blood pressure more effectively during the day than during the night.

A further example is in the administration of non-steroidal anti-inflammatory drugs to treat arthritis. It is common to have morning joint stiffness in arthritis, and the delayed release system can be taken at bedtime to deliver the drug just before waking and achieve a maximal benefit for the patient.

The delayed release dosage form can also be explored to deliver two dosages in a single dosage form in a form of pulsatile profile in which a high active concentration combined with a low concentration trough is desirable. An immediate release drug formulation can be either coated onto or directly filled with the delayed release dosage form into a single capsule. The first immediate release part of the drug will be made available soon after the capsule is taken. The second part of the dose will be made available after the predetermined delay time in either a rapid or controlled release manner. Diltiazem hydrochloride and methylphenidate hydrochloride are among other drugs recommended for a pulsatile profile.

This approach may also be applied to deliver anti-emetic drugs for postoperative sickness. The delayed release dosage form can be given as a pre-medication before the operation when the patient is not vomiting, to release the drug when it most needed A delayed release dosage form might also find a major application for colonic drug delivery. Drug delivery to the colon has advantages for local effects, such as the topical treatment of diseases such as irritable bowel syndrome, ulcerative colitis, Crohn's disease, colon carcinoma and many bacterial and helminthes infections. A 3 to 4 hour transit time through the small intestine appears to be independent of the physiological condition or the type and quantity of the food present, see Davis et al. International Journal of Pharmaceutics 21 (1986) 167-177. For colonic delivery, the main aim is to ensure the site of release, rather than the time of release. To this end the formulations of this invention such as the multiparticulates will typically have an additional, enteric coat. In this respect, the duration of passage of multiparticulates through the stomach can be highly variable, but the time of transit through the intestinal tract is more predictable. Therefore, the enteric coat might dissolve in about 1 hour after the multiparticulates leave the stomach, and the delayed release coat can then provide a time delay of say two or three hours beyond that. The time taken to reach the ileocoacal region, essentially the junction of the small intestine and the colon, is about three to four hours, so the multiparticulates with enteric coating can ensure delivery to the colon. The delay given by the enteric coating can be varied by applying different weights of the enteric coat, as well as by varying the nature of the coat.

Several corticosteroids such as budesonide, fluticasone, and prednisolone sodium metasulphobenzoate are the first line treatments of acute and recurrent of inflammatory bowel diseases, especially in treatment of ulcerative colitis and Crohn's disease. Like other steroids, they are not sufficiently site-specific, with a wide variety of side effects due to systemic absorption. The small intestine is the major site of drug absorption. Avoiding drug release in the small intestine might either completely eliminate or significantly reduce system absorption. The above selected drugs possess low systemic absorption, in particular in the colon region. Introducing these drugs in the delay release technology will further reduce the systemic absorption and hence lower side effect.

Budesonide solid dosage form is available as spheroids in capsules. From the composition of the non-active contents it is believed that the product is formulated as sustained release and over coated with enteric coat. It has been reported that 68% and 69% of the total absorbed Budesonide, from this formulation, was in the ileum and ascending colon in 8 fasting and fed healthy subject respectively. The recommended daily dose for induction of remission is 9 mg once a day in the morning for up to 8 weeks.

Fluticasone Propionate is another steroid candidate and is currently used for management of asthma and was used by mouth in the treatment of Crohn's disease and ulcerative colitis. Due to the low bioavailability, Fluticasone was reported to be able to exert topical anti-inflammatory action without any, or with minimum, side effect. The recommended oral dose for Fluticasone is 5 mg four times a day for non-specific delivery system. Lower dose or frequency may be recommended for delay release system.

Prednisolone sodium metasulphobenzoate (PSMB) is a prednisolone analogue recently tested in colonic delivery device in the treatment of irritable bowel syndrome diseases. PSMB is a very polar compound, which is poorly absorbed with a very low bioavailability. PSMB is available in the market for the treatment of ulcerative colitis and Crohn's disease in the form of liquid enema and foam for rectal application. The recommended dose is equivalent to 20 mg prednisolone. Prednisolone sodium metasulphobenzoate 157 mg is approximately equivalent to 100 mg prednisolone.

The low to moderate dose strength of the three above corticosteroids (3, 5, and 32 mg of budesonide, fluticasone, and PSMB respectively) makes them prime potential candidates for the delay release technology of this invention. 1 to 50%, for example 10-20% drug load in the spheroid cores leads to higher level of other essential additives such as spheronization aids and disruption agent to improve the quality of the spheroids and to enhance the prompt and complete release of the drug after the determined time.

Although time delayed single unit dosage forms such as tablet and capsules are easier to develop, multiunit dosage forms such as multiparticulates, beads and spheroids in particular have pronounced pharmaceutical advantages which include:
optimum flow
efficient blending
effective coating,
reproducible encapsulation and tabletting
In addition they offer many therapeutic advantages:
uniform transit through the gastrointestinal tract, unaffected by the physiological condition and of the fed or fasting state of the subject,
lower risk of dose dumping,
less irritant of the gastrointestinal tract,
the drug release covers wider area at the absorption site.

Gastric emptying of dosage forms is highly variable depending on the physiological condition, fed or fasting state, and on the shape, size and physical state of the dosage form.

The preferred multiunits can be produced by extrusion spheronisation, which is well known to those skilled in the art. Typically materials which are suitable for mechanical disruption are not easy to spheronise since they swell and expand dramatically on wet massing. Here we use a combination with a polymer to act as a binder and rounding agent for example HPMC, PVP. Binding agents can be first dissolved in water or dry blended with the other ingredients before wet massing.

The difficulties of achieving sufficient mechanical stress to rupture the coat in a multiunit with a large surface area:volume ratio are overcome by processing to maximise the wet spheroid size and minimise the dry spheroid size. Spheroids are typically 0.5-1.5 mm diameter, however for the purposes of this invention an upper size range 1.0-2.0 mm is more preferable to achieve a smaller surface area: volume ratio. To achieve the upper size range, especially in the presence of the expansion agent, larger extrudates are required. Therefore larger diameter extruder holes were required for example 1.3-2.0 mm diameter (the maximum size is estimated to be 3 mm).

After the process of wet massing and extrusion, due to hydration/expansion of the polymers, the spheroids are made at their maximum size. On drying, the large spheroids contract to a smaller fixed size. To ensure the wet spheroids contract to the smallest possible size a low rate drying process is necessary to avoid crust formation, which could restrict the natural smooth contraction process. Fast drying leads to larger spheroids with large voids within the structure. In this latter case hydration expansion will be at the expense of the voids rather than the total volume of the sphere.

By including a binder into the core formulation, extruding to a larger diameter and drying in a manner to ensure maximum shrinkage of the spheroids we are uniquely able to process the mechanical disrupting agents and provide the necessary disruptive forces normally associated with larger single units. Additionally the novel coating combination of a highly viscous water soluble polymer and a water insoluble film former provides sufficient delay to the release whilst still being able to be broken down by the mechanical forces of the core.

Conventional extrusion spheronization technology was adopted to produce multiunit spheroid cores. Other technologies such as drum/pan granulation or Glatt rotary granulator/coater and drug loading on sugar beads can also be used for the spheroid cores manufacturing.

The first stage of spheroid cores preparation is dry blending of the ingredients in a planetary or high shear mixer such as Gral or Vactron. The dry blend is then massed by the gradual addition of the binder (usually water). The wet mass is then fed through an extruder for example Alexanderwerk however, single and twin screw extruders, Caleva extruder and Nica (screen type) extruders can be equally used to manufacture the spheroid cores. Shaping of the extrudate into round spheroids is accomplished by placing the extrudate on the spinning plate of a spheroniser for example Caleva, although other spheronisers such as the Nica can be used. The spheronisation time, spheronisation speed and the loading weight effect the quality and the yield of the spheroids. The wet spheroid cores are dried in a fluid bed drier for example aeromatic although other drying methods such as oven or microwave can be used. Application of the film coat is achieved by spray coating in a fluid bed drier.

Factors that could have a significant effect on the quality of the manufactured spheroid cores and/or the quality and uniformity of the coat are as follows:

Dry blending and wet massing influences the content uniformity and also the plasticity of the mass. Blending time, water quantity and the method of addition are major factors on the quality of the spheroid cores along with the spheronization time, speed and load.

Drying of the spheroids should be started at a low rate to avoid crust formation and hence high porosity low density cores; 20-60° C. preferably 30-40° C. starting temperature followed by 60-100° C. preferably 40-80° C. are ideal conditions for drying the expanded spheroids. Fast drying leads to larger spheroids with large voids within the structure and as a result, the expansion from hydration will be at the expense of the voids rather than the total volume of the spheroid.

In the coating process, inlet, outlet and product temperature affect the quality and uniformity of the coat; 30-80° C. preferably 40-60° C., 20-50° C. preferably 25-35° C. and 20-40° C. are desirable for inlet, outlet and product temperature respectively.

Atomizing air 0.5-3 bar, preferably 1-2 bar, fluidisation air, 50-300 m$^3$ preferably 70-150 m$^3$ and spray rate of 5-100 preferably 10-70 g/min/kg spheroid load are the optimum conditions for effective and uniform coating.

EXAMPLES OF THE INVENTION

The present invention is illustrated by the following non-limiting examples.

DESCRIPTION OF THE DRAWINGS

The examples refer to the accompanying drawings, in which.

EXAMPLE 1 a. Expansion Spheroid cores, batch code F667/101: (table 1)
Cores were made by dry blending and wet granulation of the following ingredients.

| Item | Role | Percentage |
| --- | --- | --- |
| low substituted hydroxypropylcellulose LH-20 | expanding agent | 35.0 |
| diltiazem hydrochloride | drug | 10.0 |
| HPMC high viscosity grade | binder | 0.5 |
| Avicel PH101 | spheronization aid | 54.5 |

Purified water was used as granulating fluid (1.69 kg/kg solids)

The dry blending and wet granulation was carried out in Collette Gral 10 high shear mixer for 5 and 9 minutes respectively. The amount of granulating fluid used was 1.69 kg per kg solid and was added gradually over 3 minutes.

The wet mass was extruded using an Alexanderwerk extruder provided with 1.3 mm diameter perforated cylinder. The extrudates were then spheronised into 1.3 mm mean diameter size spheroids using a Caleva Model 15G spheroniser run at a loading of 0.4 kg and at 800 rpm for 6 minutes.

Drying was carried out in Aeromatic Strea 1 at an inlet temperature of 40° C. for the first 30 minutes of drying to minimize crust formation and to ensure full contraction of the cores and continued at 60° C. for 105 minutes to a constant weight.

b. Delay release coating of the Spheroid cores: (table 2).

| Ingredient | Role | Percentage |
|---|---|---|
| diltiazem cores | core | F667/101 |
| ethyl cellulose N10 | film forming water insoluble polymer | 4.0 |
| HPMC K100M | gel forming water soluble polymer | 3.3 |
| triethyl citrate | plasticiser | 0.2 |
| methylene chloride | solvent | 37.1 |
| methanol B.P. 1973 | solvent | 55.4 |

In the coating solution, a 55:45 ratio of film forming (water insoluble polymer) ethyl cellulose (EC): gel forming (water soluble polymer) hydroxypropylmethylcellulose (HPMC) was used. Triethyl citrate (plasticizer) and methanol/methylene chloride (solvents) were used according to the formulation in table 2

Coating was carried out using an Aeromatic Strea 1 fluid bed spray coater. The air inlet temperature was 52-56° C. and the outlet temperature was 30-34° C. The atomizing air pressure was 1.5-1.6 bar and the spray rate was 6-11 g/min. The product load was 0.350 kg.

Four different levels of coating were added to the expansion core batch F667/101. F669/06, F671/17, F671/47A and F671/47B had coatings of 3.0, 4.6, 5.5, and 6.6 kg coating solution/1.0 kg spheroid beads, respectively.

Figure 2:
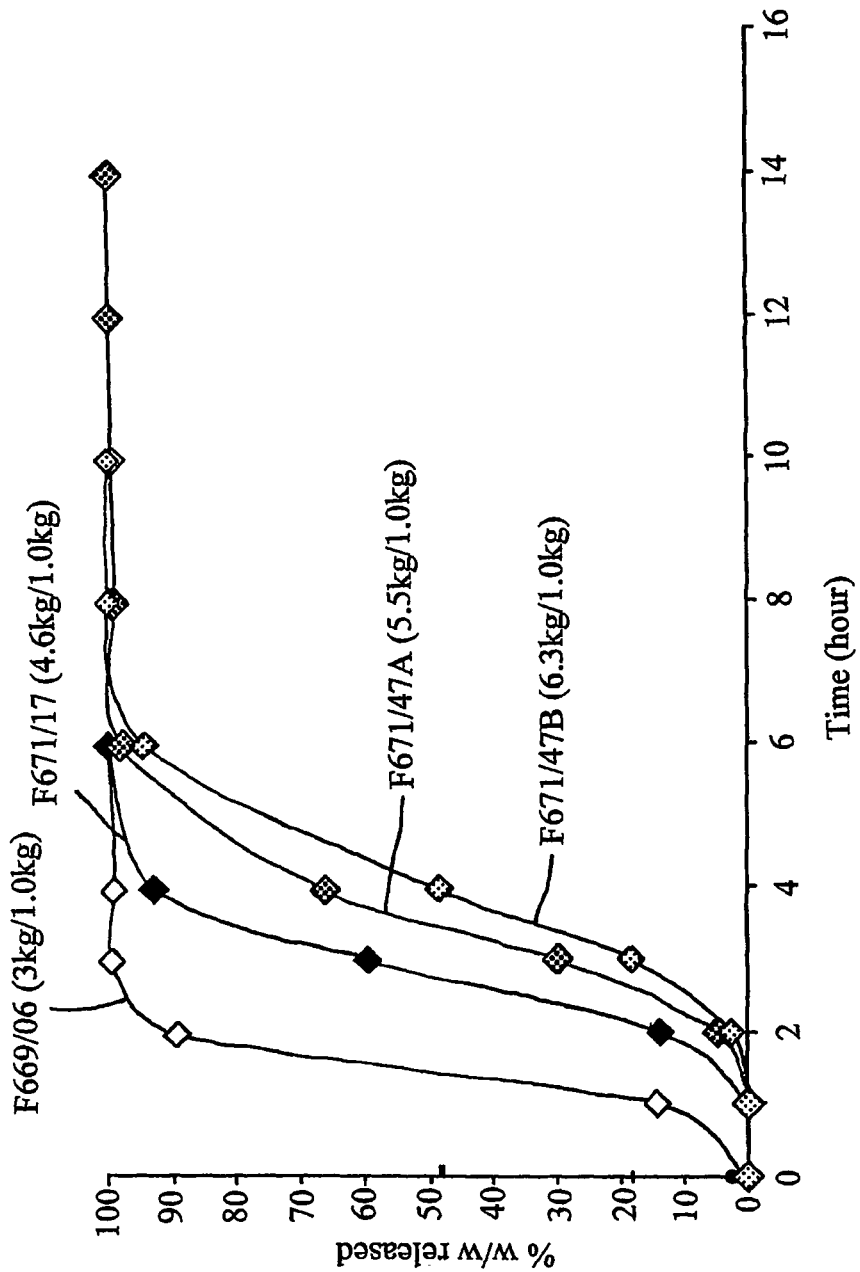
FIG. 2 shows dissolution data for products prepared in Example 1.

The dissolution rate and profile are shown in FIG. 2.

Figure 7:
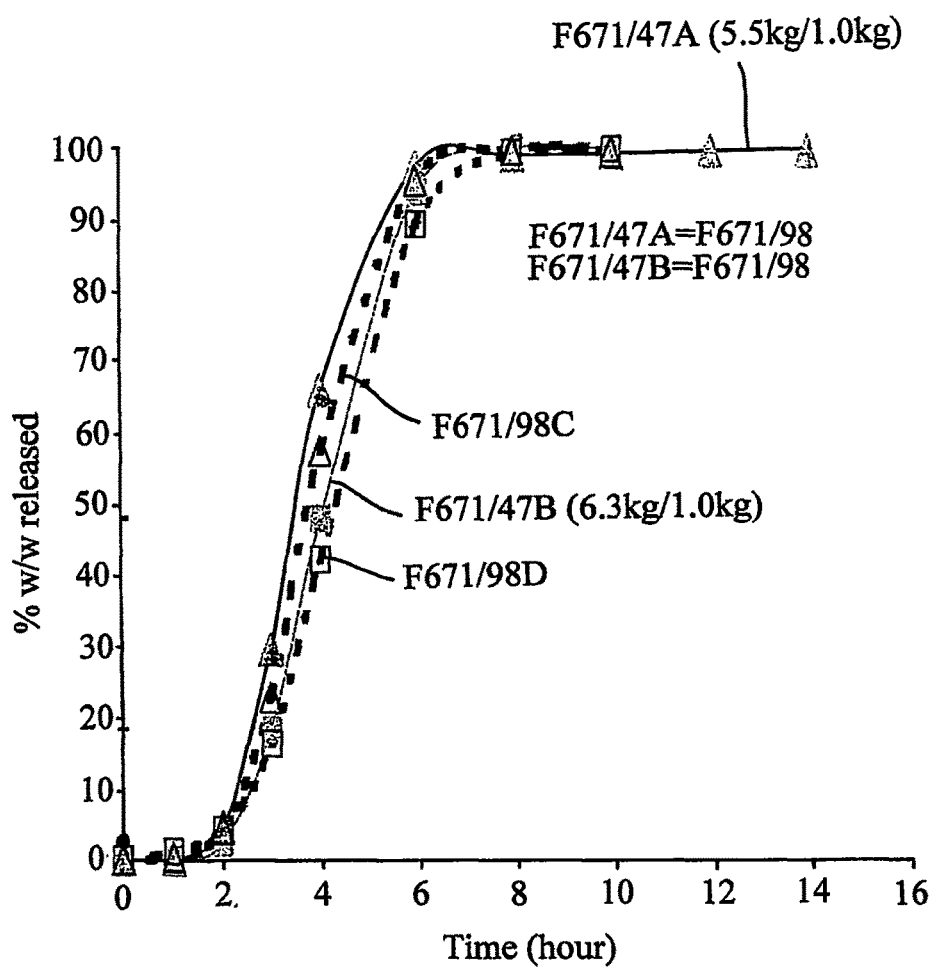
FIG. 7 shows dissolution data for products prepared in Example 1.

The procedure to prepare batch F671/47A was repeated to give a batch F671/98C. The procedure to prepare batch F671/47B was repeated to give batch F671/98D. The dissolution rate and profile for these comparative batches is shown in FIG. 7.

EXAMPLE 2 a. Expansion Spheroid cores, batch code F666/57 (table 3)

| Item | Role | Percentage |
|---|---|---|
| Explotab | expanding agent | 20.0 |
| diltiazem hydrochloride | Model drug | 20.0 |
| Avicel PH101 | Spheronization aid | 60.0 |

Purified water used as granulating fluid 0.75 kg per kg solid

An 800 g batch size was made according to table 3 above. All manufacturing processes were as that of example 1.

The spheroid cores made of the 1.00 mm diameter extrudates were at their maximum expansion stage before drying. On drying contraction took place producing spheroid cores of less than 1.00 mm mean size. The dried spheroid cores were divided according to their particle size distribution into two lots. Larger spheroid cores<1.8→0.9 mm were selected for further coating. Fine spheroid cores<0.9 mm of batch F666/57 were blended with 0.5% magnesium stearate and talc. The blended spheroid cores were then compressed into 5.0 mm normal concave tablets b. Delay release coating of the compressed spheroid cores (table 4)

| Ingredient | Role | Percentage |
|---|---|---|
| compressed diltiazem cores | core | F666/74 |
| ethyl cellulose n10 | film forming water insoluble polymer | 4.8 |
| HPMC K100M | gel forming water soluble polymer | 3.2 |
| triethyl citrate | plasticiser | 0.2 |
| methylene chloride | solvent | 30.0 |
| methanol B.P. 1973 | solvent | 61.8 |

Fine spheroid cores<0.9 mm of batch F666/57 were blended with 0.5% magnesium stearate and talc. The blended spheroid cores were then compressed into 5.0 mm normal concave tablets (F666/74). The coating solution, ethyl cellulose:HPMC (60:40) was used to coat the compressed spheroid cores at three different levels, 1.0, 2.0 and 3.0 kg/1.0 kg tablets, batch codes F666/77A, F666/77/B, and F666/77C respectively.

c. Delay release coating of spheroid cores (table 5)

| Ingredient | Role | Percentage |
|---|---|---|
| diltiazem cores | core | F666/57 |
| ethyl cellulose n10 | film forming water insoluble polymer | 4.8 |
| HPMC K100M | gel forming water soluble polymer | 3.2 |
| triethyl citrate | plasticiser | 0.2 |
| methylene chloride | solvent | 30.0 |
| methanol B.P. 1973 | solvent | 61.8 |

The larger spheroid cores of F666/57 were coated with the same coating for instance 60:40 (EC:HPMC). Two levels of coat 4.0 kg and 6.0 kg coating solution/1.0 kg spheroid cores was applied to F666/98 and F666/106 respectively.

Figure 3:
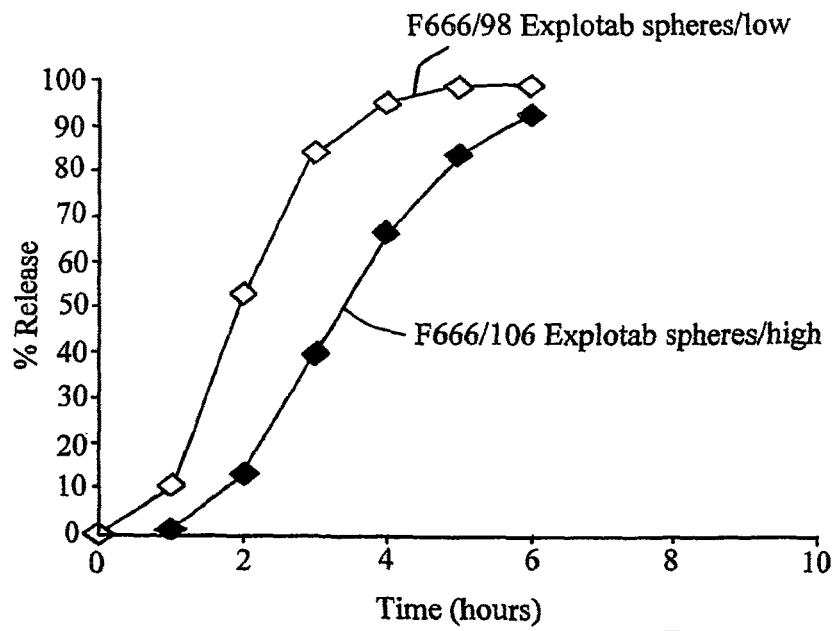
FIGS. 3 and 4 show dissolution data for products prepared in Example 2
Figure 4:
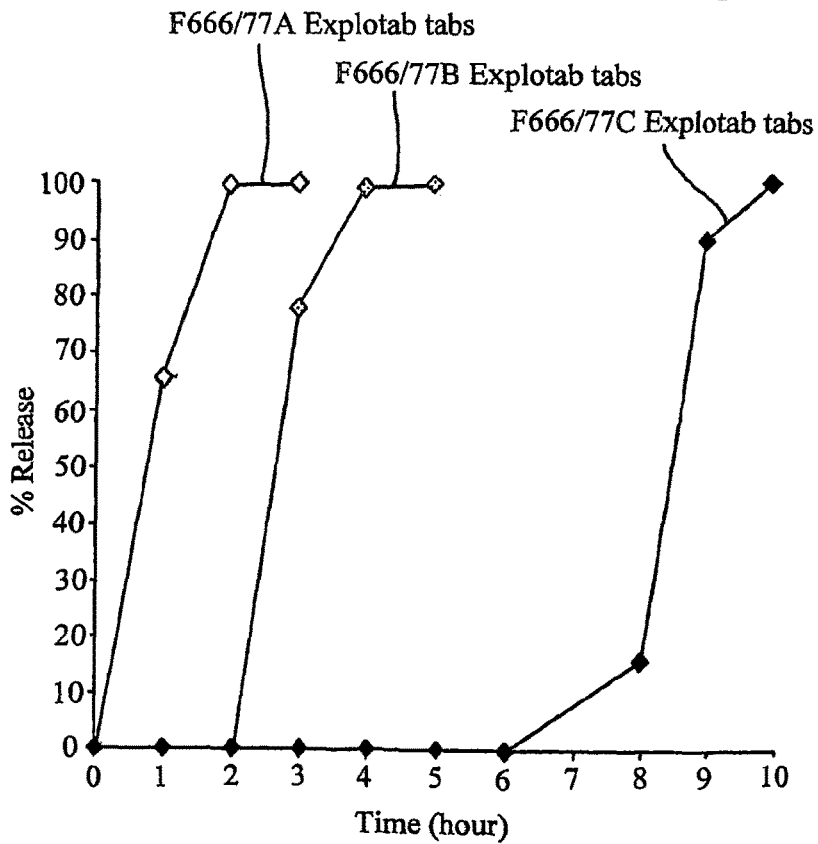

The dissolution results (FIGS. 3 and 4) clearly indicate the significant effect of the surface area/volume on the level of coat and hence on the release rate and profile.

EXAMPLE 3

Example 3 comprises immediate release osmotic spheroid cores containing diltiazem chloride as drug and a modified release coat.

a. Osmotic spheroid cores F666118 (table 6)

| Ingredient | Role | Percentage |
|---|---|---|
| diltiazem HCl | model drug | 20.0 |
| Avicel PH101 | spheronization aid | 65.0 |
| NaCl | osmotic agent | 15.0 |

Purified water 0.68 kg/kg solid was used for granulating

A batch of spheroid cores 800 g was made with 15% osmotic agent sodium chloride, 20% drug load and 65% spheronization aid microcrystalline cellulose (F666/18). The processing was as for example 1.

The dry blending and wet granulation was carried out in Collette Grall 10 high shear mixer for 5 and 6 minutes respectively. Moulding (extrusion) was performed using the Alexanderwerk extruder provided with 1.0 mm diameter perforated cylinder. The extrudates were then spheronised into 1.0 mm mean size spheroids.

Drying was carried out in Aeromatic Strea 1 at an inlet temperature of 60° C. for 105 minutes to a constant weight.

b. Delay release coating (table 7)

| Ingredient | Role | Percentage |
|---|---|---|
| diltiazem cores | core | F666/18 |
| ethyl cellulose n10 | film forming water insoluble polymer | 4.8 |
| HPMC K100M | gel forming water soluble polymer | 3.2 |
| triethyl citrate | plasticiser | 0.2 |
| methylene chloride | solvent | 30.0 |
| methanol B.P. 1973 | solvent | 61.8 |

In the coating solution, 60:40 film-forming water-insoluble polymer ethyl cellulose (EC): the water-soluble gel-forming polymer hydroxypropylmethylcellulose (HPMC) was used. Triethyl citrate (plasticiser) and methanol/methylene chloride were used according to the formulation in table 7 above.

A total of 1.4 and 4.2 kg coating solution/1.0 kg spheroid cores were applied for F666/46 and F666/65 respectively.

Figure 5:
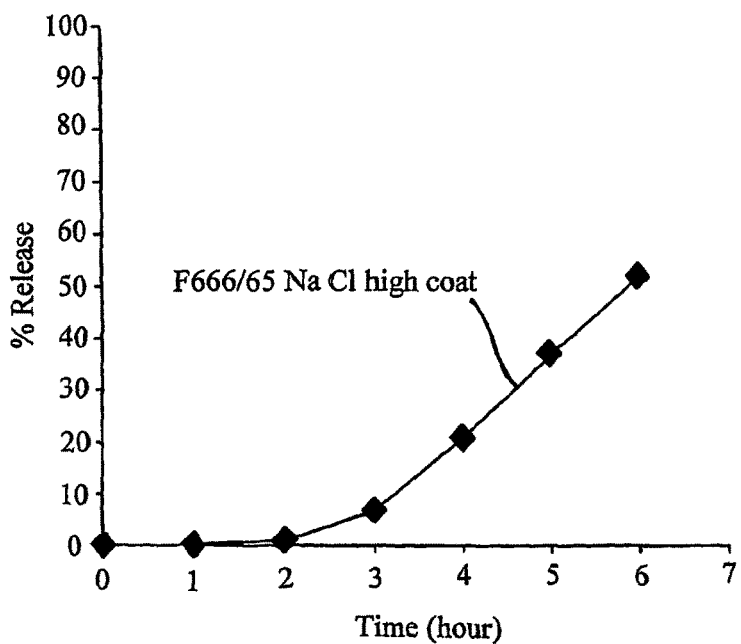
FIG. 5 shows dissolution data for products prepared in Example 3.

While almost all drug released in the first hour of the low coating batch (F666/46), the two hours time delay followed by a rapid release required by the invention was seen at a high coating level batch (F666/65) (FIG. 5).

EXAMPLE 4 a. Expansion spheroid cores: (table 8) F667/43

| Ingredient | Role | Percentage |
|---|---|---|
| diltiazem HCl | model drug | 10.0 |
| Avicel PH101 | spheronization aid | 59.5 |
| LH-20 | osmotic agent | 30.0 |
| HPMC K100M | binder | 0.5 |

One batch of spheroid cores 800 g batch size (F667/49) was made of 30% w/w low substituted hydroxypropylcellulose (LH-20), 10% w/w diltiazem hydrochloride, 0.5% high viscosity grade HPMC and 59.5% Avicel PH101. The manufactured batch was divided into two equal sub-batches for coating with two different coating solutions. Each sub-batch was coated separately under same condition applying two different coating solutions b. Delay release coating of the spheroid cores (60:40): (table 9).

| Ingredient | Role | Percentage |
|---|---|---|
| diltiazem cores | core | F666/43 |
| ethyl cellulose n10 | film forming water insoluble polymer | 4.8 |
| HPMC K100M | gel forming water soluble polymer | 3.2 |
| triethyl citrate | plasticiser | 0.2 |
| methylene chloride | solvent | 30.0 |
| methanol B.P. 1973 | solvent | 61.8 |

The first batch (F667/50) was coated with the coating solution shown above. The coating solution was made of 60:40 film-forming water-insoluble polymer (ethyl cellulose): gel-forming polymer (high viscosity grade HPMC). A total of 4.0 kg coating solution/1.0 kg spheroid cores was added.

c. Delay release coating of the spheroid cores (50:50): (table 10).

| Ingredient | Role | Percentage |
|---|---|---|
| diltiazem cores | core | F666/18 |
| ethyl cellulose n10 | film forming water insoluble polymer | 4.0 |
| HPMC K100M | gel forming water soluble polymer | 4.0 |
| triethyl citrate | plasticiser | 0.2 |
| methylene chloride | solvent | 30.0 |
| methanol B.P. 1973 | solvent | 61.8 |

The second batch was coated under identical condition with a lower ratio of the film-forming polymer, 50:50 ratio of film-forming water-insoluble polymer (ethyl cellulose): gel-forming polymer (high viscosity grade). The same coating level was applied, a total of 4.0 kg coating solution/1.0 kg spheroid cores.

Figure 1:
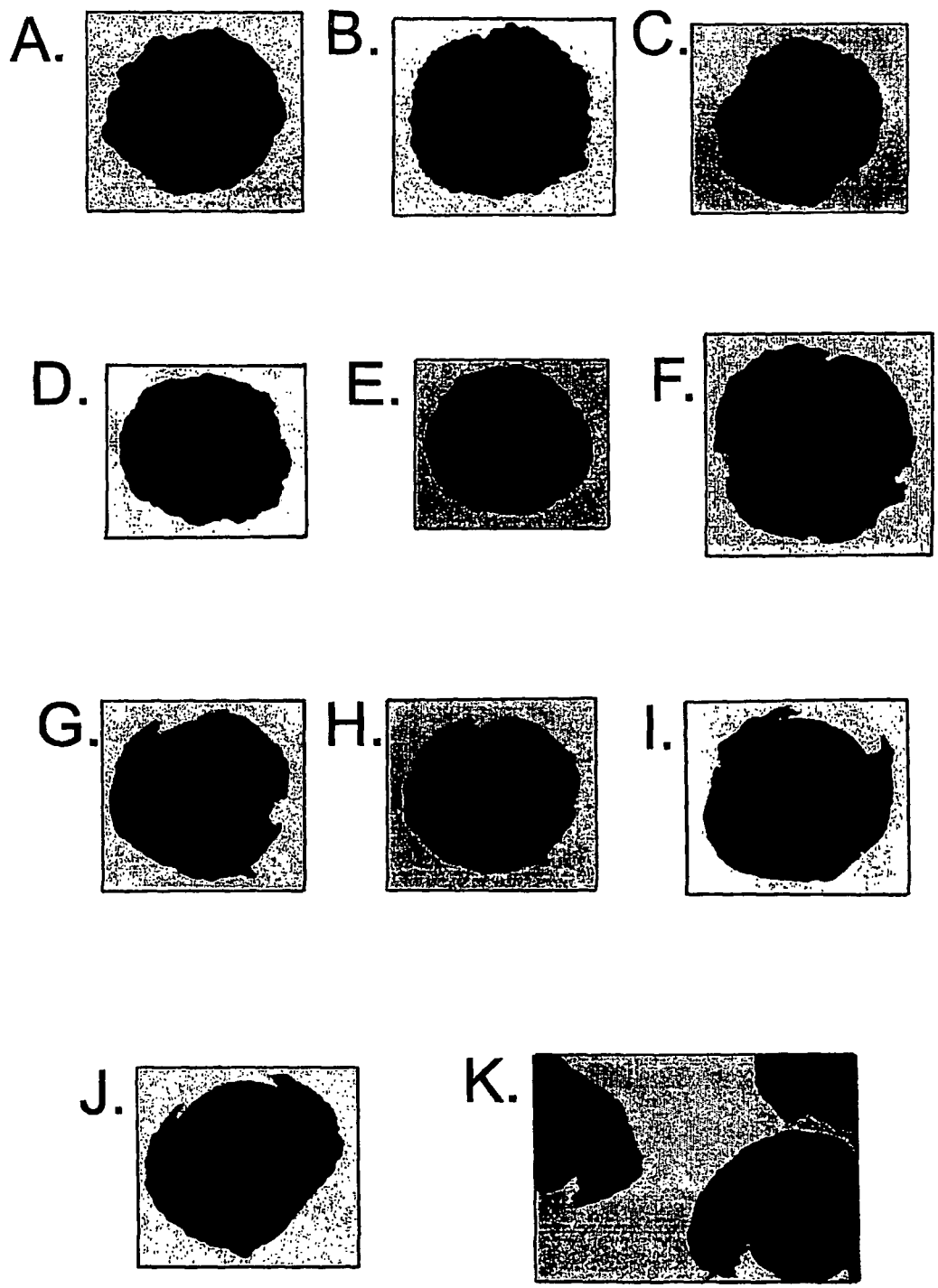
FIG. 1:*i* and 1:*ii* comprise a set of photomicrographs following the hydration of a coated product referred to in Example 4.
Figure 6:
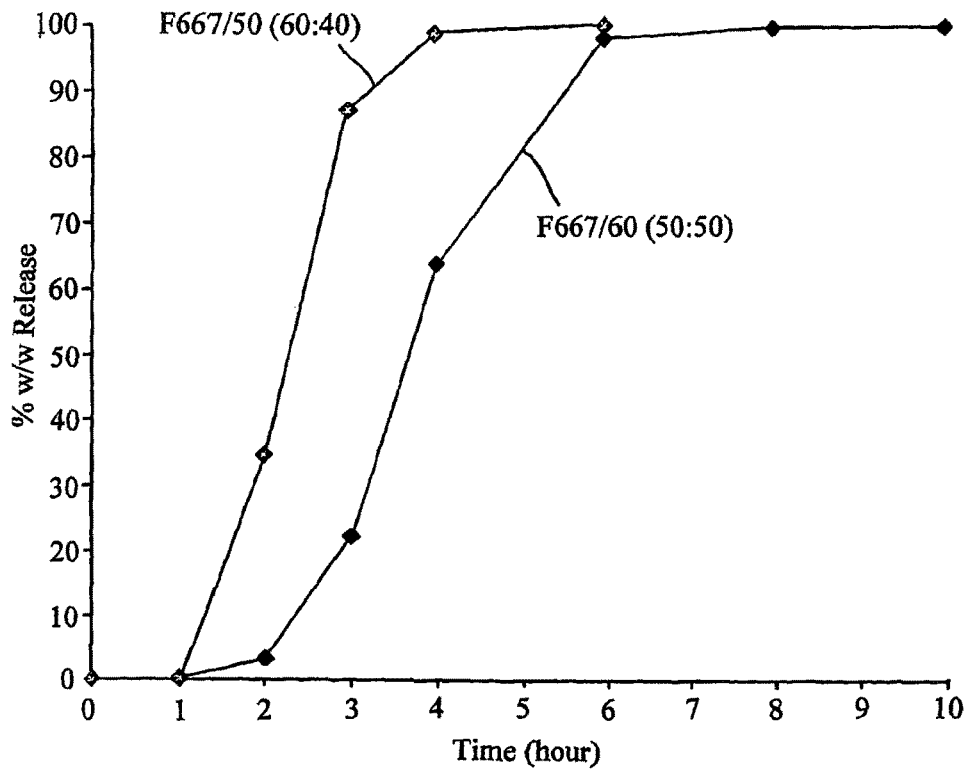
FIG. 6 shows dissolution data for products prepared in Example 4.

The release rate and profile were significantly different for the two batches. The higher the ratio of film forming polymer (ethyl cellulose) the longer the delay time observed for the same amount of coat (FIG. 6). The expansion and mechanical disruption of the product F667/76 which is F667/50 with an extra 1.5 kg of coating solution additional to that for F667/50 is shown in the photomicrographs of FIGS. 1:$i$ and 1:$ii$. The photomicrographs were taken of the hydrating multiunits at room temperature gently agitated in 50 ml purified water, where:

A is the dry sphere;
B is dry sphere washed with water;
C is 15 minutes in water;
D is 45 minutes in water;
E is 75 minutes in water;
F is 90 minutes in water;
G is 180 minutes in water;
H is 180 minutes in water/dried;
I is 240 minutes in water;
J is 330 minutes in water;
K is 24 hours in water/dried.

EXAMPLE 5

A coated spheroid formulation for 5-aminosalicylic acid is made for colonic delivery.

The ingredients for the spheroids are as follows:

|  | % w/w |
|---|---|
| 5-aminosalicylic acid | 50.0 |
| microcrystalline cellulose Ph. Eur Avicel PH101 | 24.75 |
| HPC LH20 | 24.75 |
| HPMC K100M | 0.5 |
| Purified water Ph. Eur | qs |

Spheroids are made from these ingredients in a manner similar to the preceding examples. The spheroids are given a delayed release coating using the following ingredients.

|  | % w/w |
|---|---|
| ethylcellulose N10 USNF | 4.03 |
| methocel K100M | 3.30 |
| triethyl citrate | 0.22 |
| methylene chloride | 37.07 |
| methanol BP 1973 | 55.38 |

The spheroids with the delayed release coating are then given an enteric coating using the following ingredients.

| | weight |
|---|---|
| Eudragit L 30D-55 USNF (30% solids) | 24.1 |
| triethyl citrate USNF | 1.40 |
| talc Ph Eur | 2.40 |
| purified water Ph Eur | 20.7 |

The water is placed in a suitable container and the talc and triethyl citrate are slowly added using a suitable high speed mixer/emulsifier to give a lump-free dispersion. The Eudragit suspension is sieved using a 0.25 mm sieve and mixed using a high speed paddle mixer. The mix is then gradually added to the lump-free dispersion and mixing is continued during the coating process.

EXAMPLE 6

A hypnotic-active formulation is prepared in a manner similar to Examples 1 to 4 using 5-10 mg Zolpidem tartrate and 7.5-15 mg Zolpiclone, giving a delay of 2 to 3 hours before the onset of release.

EXAMPLE 7

Further work was carried out on formulations of 5-aminosalicylic acid, (5ASA), for colonic delivery.

50-60% 5ASA was loaded on the cores with the spheronisation aid, microcrystalline cellulose (Avicel PH 102); the disruption aid, low substituted hydroxypropyl cellulose (LH20); and the binder, high viscosity grade hydroxypropylmethylcellulose, (HPMC). Low level binder (less than 1.0%) is required to improve the quality of the spheroids. Several batches of cores were manufactured and individually coated with different coating solutions. Both HPMC K100M and HPMC K4M and the combination of the two were investigated. Coating solutions of 40:60, 50:50 and 60:40 ratios of ethyl cellulose (EC): HPMC were tested. In addition one core batch was divided into three sub batches based on their particle size distribution. The three batches selected were: >1.4-<1.6 mm <2.0 mm and >2.0 mm.

Several examples of the core formulation and coating solution formulation together with drug release from the final spheroids products are presented below.

A—Spheroid cores, 50% drug load, different coat levels.

| Core formulation (F676/30) | |
|---|---|
| Material | weight |
| 5 ASA | 50.0 |
| Avicel PH101 | 25.75 |
| HPC LH20 | 24.75 |
| HPMC K100M | 0.5 |

| Coat formulation* (F676/49A, B, C, F676/59) | |
|---|---|
| Material | % w/w |
| Ethyl Cellulose | 4.03 |
| HPMC K100M | 3.30 |
| Triethyl Citrate | 0.22 |
| Methylene Chloride | 37.07 |

*Theoretical weight gains are 5.7, 11.3, 13.7, 17.6% w/w for F676/49 A, B, C and F676/59 respectively.

B—Spheroids cores, 60% drug load, different HPMC grades

| Core formulation (F676/66) | |
|---|---|
| Material | % w/w |
| 5 ASA | 60.0 |
| Avicel PH101 | 19.75 |
| HPC LH20 | 19.75 |
| HPMC K100M | 0.5 |
| Methanol | 62.34 |

| Coat formulations (F676/72B, F676/95B, F676/105B) | | | |
|---|---|---|---|
| Material | % w/w | | |
| Ethyl Cellulose | 4.0 | 4.0 | 4.0 |
| HPMC K100M | 4.0 | 2.0 | — |
| HPMC K4M | — | 2.0 | 4.0 |
| Triethyl Citrate | 0.24 | 0.24 | 0.24 |
| Methylene Chloride | 30.0 | 30.0 | 30.0 |
| Methanol | 61.8 | 61.8 | 61.8 |

Coated to same theoretical weight gain of 27% w/w.

C—Different particle size distribution

| Core formulation (F676/58) | |
|---|---|
| Material | % w/w |
| 5 ASA | 60.0 |
| Avicel PH101 | 9.75 |
| HPC LH20 | 29.5 |
| HPMC K100M | 0.75 |

| Coat formulation (F687/59 (>1.6-<2.0 mm), F687/66 (>2.0 mm), F687/73 (>1.4-<1.6 mm)) | |
|---|---|
| Material | % w/w |
| Ethyl Cellulose | 3.51 |
| HPMC K100M | 3.51 |
| Triethyl Citrate | 0.21 |
| Methylene Chloride | 30.26 |
| Methanol | 55.38 |

D—Spheroid cores, 60% drug load, coated with delayed release (DR) and enteric coat(EC).

| Core formulation (F687/58A) | |
|---|---|
| Material | % w/w |
| 5 ASA | 60.0 |
| Avicel PH101 | 9.75 |
| HPC LH20 | 29.5 |
| HPMC K100M | 0.75 |

| DR formulation (F687/83) | |
|---|---|
| Material | % w/w |
| Ethyl Cellulose | 3.51 |
| HPMC K100M | 3.51 |
| Triethyl Citrate | 0.21 |
| Methylene Chloride | 30.26 |
| Methanol | 62.34 |

| EC formulation (F676/81A) | |
|---|---|
| Eudragit L30D-55 | 49.6 |
| Triethyl citrate | 2.3 |
| Talc | 4.9 |
| Water | 43.1 |

Figure 8:
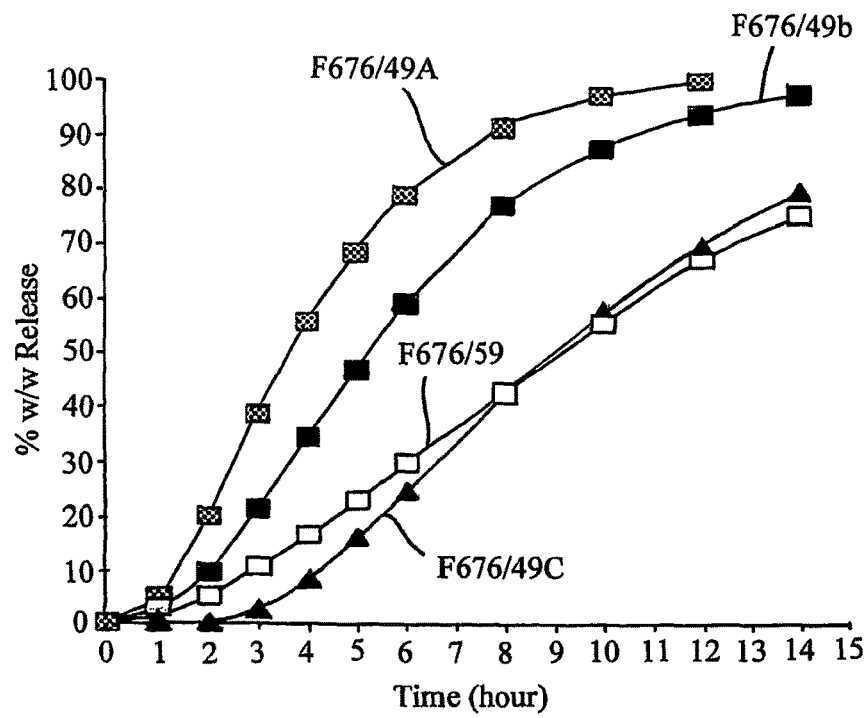
FIGS. 8 to 11 show dissolution data for products prepared in Example 7.
Figure 9:
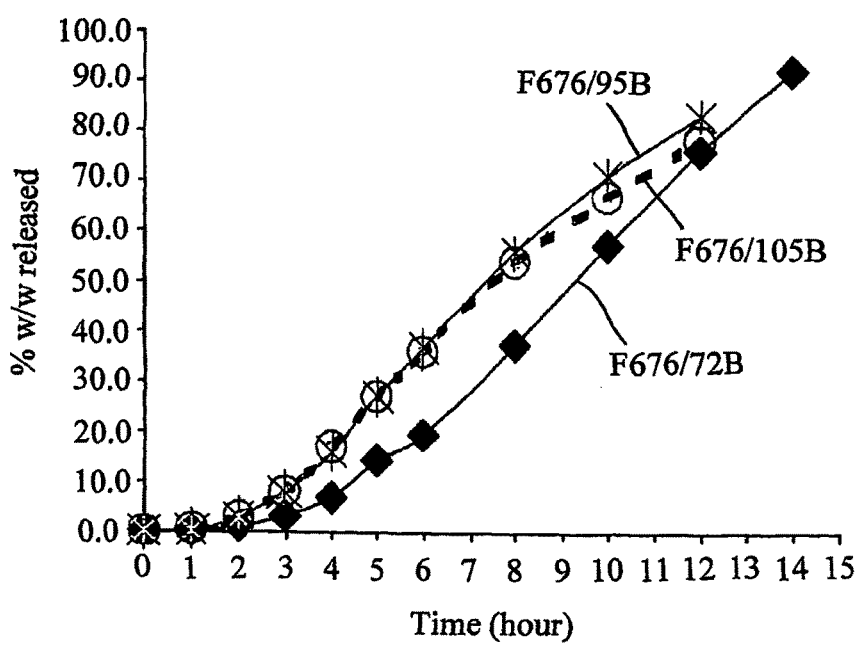
Figure 10:
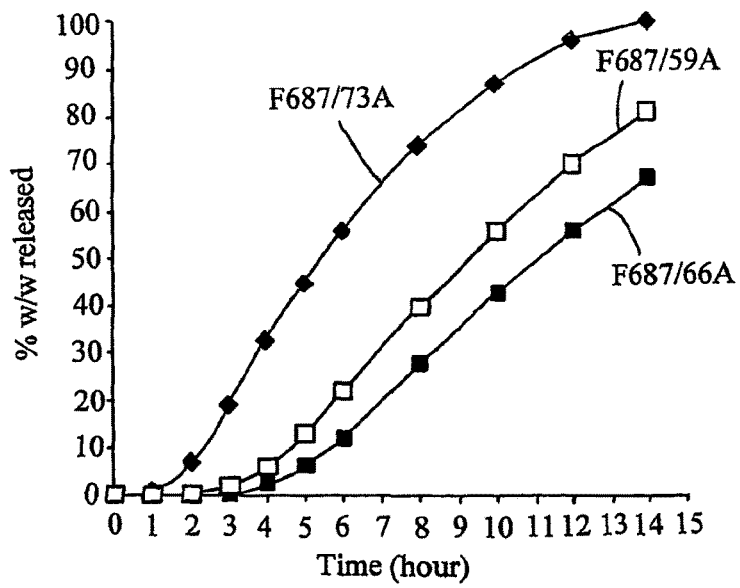
Figure 11:
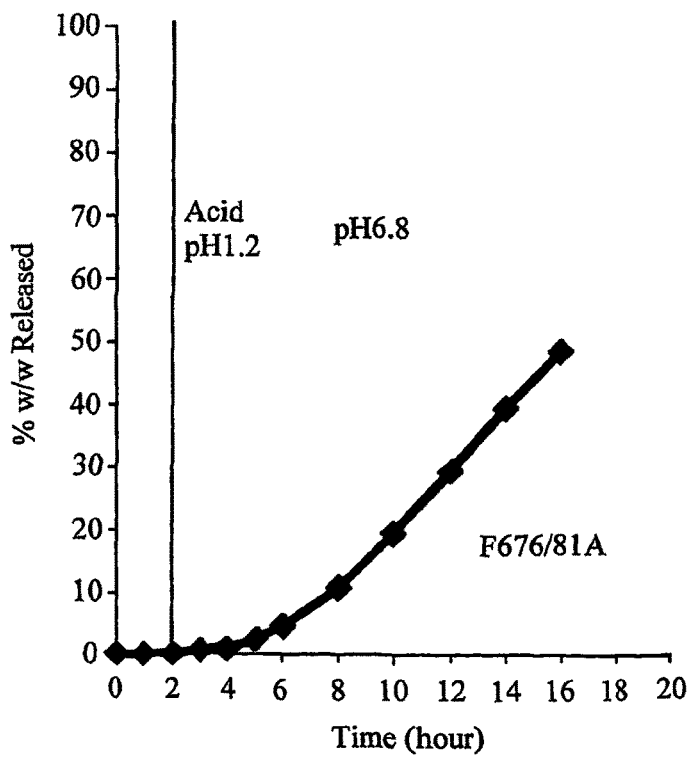

The percent release w/w of the 5ASA over time was measured for the various products, and plotted to give FIGS. 8 to 10. For FIG. 11, the dissolution profile in pH 1.2 and pH 6.8 is shown.

EXAMPLE 8

For steroids such as budesonide, fluticasone and prednisolone sodium metasulphobenzoate, typical formulations are as follows:

Spheroid Cores:

| | % w/w |
|---|---|
| Steroid (Active) | 1-50 |
| Avicel PH101 (Spheronisation aid) | 30-70 |
| HPC LH-20 (Disruption agent) | 30-70 |
| HPMC high viscosity grade (Binder) | 0-1 |

Coating Solution:

| | % w/w Film forming water-insoluble polymer:Gel forming water-soluble polymer | | |
|---|---|---|---|
| | 40:60 | 50:50 | 60:40 |
| Ethyl Cellulose | 3.2 | 4.0 | 4.8 |
| HPMC high viscosity grade K100M/K4m | 4.8 | 4.0 | 3.2 |
| Triethyl citrate | 0.24 | 0.24 | 0.24 |
| Methylene chloride | 30.0 | 30.0 | 30.0 |
| Methanol | 61.8 | 61.8 | 61.8 |

The invention claimed is:

1. A delayed release pharmaceutical composition which provides a lag in delivery of a drug following, administration, the composition comprising a multi-unit dosage of multiparticles, each unit of the composition comprising
   (a) a core which includes a drug and a disruption agent and
   (b) a regulatory membrane coating on the core formed from a mixture of a water-soluble gel-forming polymer and a water-insoluble film-forming polymer;
   wherein said water-soluble gel-forming polymer is a high viscosity grade hydroxyalkylcellulose or methyl cellulose, said water-insoluble film-forming polymer is an alkyl cellulose, and
   wherein there is a coating weight gain of said regulatory membrane coating of between 20% and 100%, and
   wherein said composition releases less than 10% of the drug in the lag period of up to 1 to 6 hours, and after said lag period, releases more than 90% of the drug over a release period of not greater than 6 hours.

2. The composition according to claim 1, wherein the disruption agent is selected from polymers which expand on hydration and compounds which generate an internal osmotic pressure within the membrane.

3. The composition according to claim 2, wherein the disruption agent is one or more of a low substituted hydroxypropylcellulose, sodium starch glycolate, sodium carboxymethylcellulose, croscarmellose sodium or carbomer.

4. The composition according to claim 2, wherein the disruption agent is one or more electrolytes, sugars or polyhydric alcohols.

5. The composition according to claim 4, wherein the core includes one or more excipients.

6. The composition according to claim 5, wherein the core is a spheroid and includes a spheronisation aid.

7. The composition according to claim 6, wherein the spheronisation aid is microcrystalline cellulose.

8. The composition according to claim 6, wherein the spheroid further includes a binder.

9. The composition according to claim 8, wherein the binder is a hydroxypropylmethylcellulose.

10. The composition according to claim 1, wherein the amount of drug is 0.1 to 500 mg.

11. The composition according to claim 1, wherein the water-soluble gel-forming polymer is a high viscosity grade hydroxypropylmethylcellulose.

12. The composition according to claim 1, wherein the alkylcellulose is ethyl cellulose.

13. The composition according to claim 1, wherein the lag period is up to 1 to 2 hours.

14. The composition according to claim 1, wherein the drug is selected from the group consisting of hypnotics, anti-inflammatories, steroids, anthelmintics, antifungals, anti-cancers, proteins and peptides, semicarbazones, H2-blockers, asthmatic drugs, beta-blockers, calcium channel blockers, NSAIDs, and anti-emetic drugs.

15. A method for preparing the composition according to claim 1, which comprises coating the core containing the drug and the disruption agent with the mixture of the water-soluble gel-forming polymer and the water-insoluble film forming polymer.

16. A method for controlling delivery of a drug to impart a delay before release after administration, which comprises formulating a delayed release pharmaceutical composition which provides a lag in the delivery of a drug following administration,
    the composition comprising a multi-unit dosage form of multiparticles, each unit of the composition comprising
    (a) a core which comprises the drug and a disruption agent, and
    (b) a regulatory membrane coating on the core comprising a water-soluble gel-forming polymer and a water-soluble film-forming polymer,
    wherein said water-soluble gel-forming polymer is a high viscosity grade hydroxyalkylcellulose or methyl cellulose, said water insoluble film-forming polymer is an alkyl cellulose, and wherein there is a coating weight gain of said regulatory membrane coating of between 20% and 100%, and
    wherein said composition releases less than 10% of the drug in the lag period of up to 1 to 6 hours, and after said lag period, releases more than 90% of the drug over a release period of not greater than 6 hours.

17. The composition according to claim 1, wherein less than 5% of the drug is released in the lag period of up to 1 to 6 hours.

18. The composition according to claim 1, which releases less than 2% of the drug in the lag period of up to 1 to 6 hours.

19. The composition according to claim 1, wherein the ratio of water-insoluble film-forming polymer to water-soluble gel-forming polymer within the regulatory membrane coating is 10:90 to 90:10.

20. The composition according to claim 1, wherein the ratio of water-insoluble film-forming polymer to water-soluble gel-forming polymer within the regulatory membrane coating is 20:80 to 80:20.

21. The composition according to claim 1, wherein the drug release from the composition is pH independent.

22. The composition according to claim 11, wherein the high viscosity grade hydroxypropylmethylcellulose is hydroxypropylmethylcellulose K100M or hydroxypropylmethylcellulose K4M.

23. The composition according to claim 12, wherein the water-soluble gel-forming polymer is hydroxypropylmethylcellulose K100M or hydroxypropylmethylcellulose K4M.

* * * * *